US008362431B2

(12) United States Patent
Hudgings et al.

(10) Patent No.: US 8,362,431 B2
(45) Date of Patent: Jan. 29, 2013

(54) METHODS OF THERMOREFLECTANCE THERMOGRAPHY

(75) Inventors: Janice A. Hudgings, South Hadley, MA (US); Joseph Summers, Northampton, MA (US)

(73) Assignee: Mount Holyoke College, South Hadley, MA (US)

( * ) Notice: Subject to any disclaimer, the term of this patent is extended or adjusted under 35 U.S.C. 154(b) by 579 days.

(21) Appl. No.: 12/240,981

(22) Filed: Sep. 29, 2008

(65) Prior Publication Data

US 2009/0084959 A1    Apr. 2, 2009

Related U.S. Application Data

(63) Continuation-in-part of application No. 11/376,722, filed on Mar. 15, 2006, now Pat. No. 7,429,735.

(60) Provisional application No. 60/661,832, filed on Mar. 15, 2005.

(51) Int. Cl.
    *G01J 5/02*    (2006.01)
    *G01J 5/06*    (2006.01)
(52) U.S. Cl. ..................................... 250/341.8; 250/340
(58) Field of Classification Search ............... 250/341.8, 250/340
    See application file for complete search history.

(56) References Cited

U.S. PATENT DOCUMENTS

| 5,223,932 | A |   | 6/1993  | Thomas et al. |
| 5,286,968 | A |   | 2/1994  | Fournier et al. |
| 5,440,338 | A |   | 8/1995  | Roundy et al. |
| 5,517,352 | A | * | 5/1996  | Hill ............................... 359/368 |
| 5,711,603 | A |   | 1/1998  | Ringermacher et al. |
| 5,943,134 | A |   | 8/1999  | Yamaguchi et al. |
| 5,946,102 | A | * | 8/1999  | Holcomb ....................... 356/417 |
| 6,028,543 | A |   | 2/2000  | Gedcke et al. |
| 6,054,868 | A | * | 4/2000  | Borden et al. ................. 324/752 |
| 6,057,952 | A |   | 5/2000  | Kubo et al. |
| RE38,307  | E | * | 11/2003 | Gustafsson et al. .......... 359/385 |
| 7,429,735 | B2|   | 9/2008  | Lueerssen et al. |
| 2002/0049386 | A1 | * | 4/2002 | Yang et al. ..................... 600/476 |
| 2002/0126732 | A1 | * | 9/2002 | Shakouri et al. .............. 374/130 |
| 2003/0126732 | A1 |   | 7/2003 | Okada |
| 2003/0201922 | A1 |   | 10/2003 | Dagher et al. |

FOREIGN PATENT DOCUMENTS

| JP | 10002855   | A  | 1/1998  |
| JP | 2000310743 | A  | 11/2000 |
| JP | 2006308513 | A  | 11/2006 |
| WO | 03052366   | A1 | 6/2003  |

OTHER PUBLICATIONS

International Patent No. 03052366A1; Issue Date: Jun. 26, 2003; Abstract Only; 1 page.
"Numerical Aperture"; Wikipedia, the free encyclopedia; Date Accessed: Sep. 11, 2008; http://en.wikipedia.org/wiki/Numerical_aperture; 4 pages.

(Continued)

*Primary Examiner* — Walter L Lindsay, Jr.
*Assistant Examiner* — Jessica L Eley
(74) *Attorney, Agent, or Firm* — Cantor Colburn LLP

(57) ABSTRACT

An embodiment of a method of performing thermoreflectance measurements with an imaging system comprises: reflecting radiation from a number of points in a sample in response to an illuminating radiation while a temperature modulation is applied to the sample; acquiring digital images of the reflected radiation after the reflected radiation passes through an aperture; and deriving a map of relative reflectivity of the sample based on the digital images. At least a portion of the illuminating radiation passes through at least a portion of the sample and is reflected at a change refractive index interface.

26 Claims, 5 Drawing Sheets

OTHER PUBLICATIONS

Joseph A. Summers et al.; "High Contrast Thermoreflectance Thermography using a Nipkow Disk Confocal Microscope"; Abstract for LEOS Technical Conference to be held in Nov. 2008; 2 pages.

J. B. Pawley; Handbook of Biological Confocal Microscopy, 3rd Ed., New York: Springer (2006); 18 Pages.

P.M. Mayer et al.; "Theoretical and Experimental Investigation of the Thermal Resolution and Dynamic Range of CCD-Based Thermoreflectance Imaging"; J. Opt. Soc. of America A 24; 2007; pp. 1156-1163.

S. Dilhaire et al.; Calibration Procedure for Temperature Measurements by Thermoreflectance Under High Magnification Conditions; Appl. Phys. Lett. 84; 2004; pp. 822-824.

C. Filloy et al.; "The Contribution of Thermoreflectance to High Resolution Thermal Mapping"; Sens. Rev. 23; 2003; pp. 35-39.

J. Christofferson et al.; "Camera for Thermal Imaging of Semiconductor Devices Based on Thermoreflectance"; Proceedings of the 20th Annual IEEE Semiconductor Thermal Measurement and Management Symposium, IEEE; 2004; pp. 87-91.

D. Luerssen et al.; "2-D Thermal Imaging of the Optical Power Distribution in Photonic Integrated Circuits"; Proceedings of the Annual Meeting of the Lasers and Electro-Optics Society; Rio Mar, Puerto Rico; 2004; 2 pages.

M. Farzaheh et al.; "Temperature Profiling of VCSELs by Thermoreflectance Microscopy"; IEEE Photon. Technol. Lett. 19; 2007; pp. 601-603.

M. Farzaheh et al.; "Fiber-free Characterization of Photonic Integrated Circuits by Thermoreflectance Microscopy"; Proceedings of Quantum Electronics and Laser Science Conference; Baltimore, Maryland; 2007; 2 pages.

S. Kimura et al.; "Confocal Scanning Optical Microscope using Single-Mode Fiber for Signal Detection"; Appl. Opt. 30; 1991; pp. 2143-2150.

G. Busse et al.; "Thermal Wave Imaging with Phase Sensitive Modulated Thermography"; J. Appl. Phys. 71; 1992; pp. 3962-3965.

T.R. Corle et al.; "Depth Response of Confocal Optical Microscopes"; Opt. Lett. 11; 1986; pp. 770-772.

G. Yu et al.; "Optical Properties of Wurtzite Structure GaN on Sapphire Around Fundamental Absorption Edge (0.78-4.77eV) by Spectroscopic Ellipsometry and the Optical Transmission Method"; Appl. Phys. Lett. 70; 1997; pp. 3209-3211.

M. Gu et al.; "Three-dimensional Transfer Functions in 4Pi Confocal Microscopes"; J. Opt. Soc. Am. A 11; 1994; pp. 1619-1627.

M. Schrader et al.; "Optical Transfer Functions of 4Pi Confocal Microscopes: Theory and Experiment"; Opt. Lett. 22; 1997; pp. 436-438.

E. Betzig et al.; "Breaking the Diffraction Barrier: Optical Microscopy on a Nanometric Scale"; Science 251; 1991; pp. 1468-1470.

E. Wang et al.; "Performance Comparison Between the High-Speed Yokogawa Spinning Disc Confocal System and Single-Point Scanning Confocal Systems"; J. of Microscopy 218; 2005; pp. 148-159.

G. Chen et al.; "Heat Transfer in Nanostructures for Solid-State Energy Conversion"; Transactions of the ASME 124; 2002; pp. 242-252.

G. Chen et al.; "Recent Developments in Thermoelectric Materials"; International Materials Reviews 48; 2003; pp. 45-66.

A.R. Abramson et al.; "Interface and Strain Effects on the Thermal Conductivity of Heterostructures: A Molecular Dynamics Study"; Journal of Heat Transfer 124; 2002; pp. 963-970.

W. Liu et al.; "Thermal Conduction in AlxGa1-xN Alloys and Thin Films"; Journal of Applied Physics 97; 073710-1-6; 2005; 8 pages.

X.Y. Yu et al.; "Temperature Dependence of Thermophysical Properties of GaAs/AlAs Periodic Structure"; Applied Physics Letters 67; 1995; pp. 3554-3556.

G. Chen et al.; "A Comparative Study on the Thermal Characteristics of Vertical-Cavity Surface-Emitting Lasers"; Journal of Applied Physics 77; 1995; pp. 4251-4258.

D. Luerssen et al.; "Radial Temperature Profiling of VCSELs"; Presented at CLEO; Baltimore, Maryland; 2005; 3 pages.

R. Amatya et al.; "Thermal Lensing in Oxide-Confined, Single-mode VCSELs"; Submitted to Conference on Lasers and Electrooptics; Long Beach, California; 2006; 3 pages.

W.B. Joyce et al.; "Thermal Resistance of Heterostructure Lasers"; J. Appl. Phys. 46; 1975; 8 pages.

I. Camps et al.; "Calculation of the Thermal Resistance and Temperature Distribution in Blue-Green Semiconductor Lasers"; Semiconductor Science and Technology 12; 1997; pp. 1574-1578.

J. Kolzer et al.; "Thermal Imaging and Measurement Techniques for Electronic Materials and Devices"; Microelectronic Engineering 31; 1996; pp. 251-270.

D.G. Cahill et al.; "Thermometry and Thermal Transport in Micro/Nanoscale Solid-State Devices and Structures"; J. Heat Transfer 124; 2002; pp. 223-229.

D. Burgess et al.; "Improved Sensitivity for Hot Spot Detection Using Liquid Crystals"; 22nd Annual Proceedings on Reliability Physics; 1984; pp. 119-121.

V.J. Bruce; "Comparison of Fluorescent Microthermography to Other Commercially Available Techniques [IC Failure Analysis]"; Proceedings of the 20th International Symposium for Testing and Failure Analysis; 1994; pp. 73-80.

J. Christofferson et al.; "Thermal Measurements of Active Semiconductor Micro-Structures Acquired Through the Substrate Using IR Thermoreflectance"; Microelectronics J. 35; 2004; pp. 791-796.

V.R. Daria et al.; "High-Contrast Images of Semiconductor Sites via One-Photon Optical Beam-Induced Current Imaging and Confocal Reflectance Microscopy"; Appl. Optics 41; 2002; pp. 4157-4161.

M.S. Unlu et al.; "Near Field Optical Beam Induced Current Measurements on Heterostructures"; Appl. Phys. Lett. 67; 1995; pp. 1862-1864.

M.A.A. Neil et al.; "Method of Obtaining Optical Sectioning by Using Structured Light in a Conventional Microscope"; Opt. Lett 22; 1997; pp. 1905-1907.

Christofferson et al., "Thermoreflectance Imaging of Superlattice Micro Refrigerators," Semitherm XVII symposium proceedings, San Jose, CA, Mar. 2001; 5 Pages.

Thorne et al., "High-Resolution Thermoreflectance Microscopy", Mat. Res. Soc. Symp. Proc., vol. 738; 2003; Materials Research Society; G12.9.1-G12.9.6.

Christenson et al., "Film Sheds Light on DNA", Spie Magazine of Photonics Technologies and Applications; Jan. 2004; 3 Pages.

Gammaitoni, "Stochastic Resonance and the Dithering Effect in Threshold Physical Settings"; The American Physical Society, vol. 52; Nov. 1995; pp. 4691-4699.

Matatagui, et al., "Thermoreflectance in Semiconductors", Physical Review, vol. 176, No. 3; Dec. 15, 1968; pp. 950-960.

Dietrich Luerssen et al.; Figures 1-4 and Table 1; Obtained Feb. 18, 2005; pp. 6-10 of 12.

D. Luerssen et al.; "Nanoscale Thermoreflectance with 10K Temperature Resolution Using Stochastic Resonance"; Proceedings of the Semiconductor Thermal Measurement and Managament Symposium, San Jose, CA; 2005; 6 Pages.

S. Grauby et al.; "High Resolution Photothermal Imaging of High Frequency Phenomena Using Visible Charge Device Camera Associated with a Multichannel Lock-in Scheme"; Rev. Sci. Instrum., vol. 70; 1999; pp. 3603-3608.

Japanese Patent No. 2006308513 (A); Publication Date: Nov. 9, 2006; Abstract Only; 1 Page.

International Search Report; International Filing Date: Sep. 28, 2009; Date of Mailing: Apr. 30, 2001; 7 Pages.

Written Opinion of the International Search Report; International Filing Date: Sep. 28, 2009; Date of Mailing: Apr. 30, 2001; 5 Pages.

* cited by examiner

| TECHNIQUE | SPATIAL RESOLUTION | THERMAL RESOLUTION | TEMPORAL RESOLUTION | 2D OR 3D |
|---|---|---|---|---|
| THERMOREFLECTANCE | 150 nm | 10-25 mK | 1 ps - 1 ms | 3D |
| THERMAL CAMERA | >5 μm | 5-10 K | 100 μs | 3D |
| LIQUID CRYSTAL THERMOGRAPHY | 1 μm | 50-500 mK | 2-3 ms | 2D |
| FLUORESCENT THERMOGRAPHY | 300 nm | 10 mK | 200 μs | 2D/3D |
| SCANNING THERMAL MICROSCOPY | 30-100 nm | 1 mK | 10 μs | 2D |
| INTERFEROMETRY BASED ON THERMAL EXPANSION | 1 μm | 10 μK | 10 ns | 2D |

Fig. 1

METHODS OF THERMOREFLECTANCE THERMOGRAPHY

CROSS-REFERENCE TO RELATED APPLICATIONS

The present application is a continuation-in-part application of U.S. patent application Ser. No. 11/376,722, filed Mar. 15, 2006, which claims the benefit of U.S. Provisional Patent Application No. 60/661,832, filed Mar. 15, 2005, which are incorporated herein by reference in their entirety.

BACKGROUND

The present disclosure generally relates to systems and methods for performing confocal thermoreflectance measurements, and more particularly, to confocal thermoreflectance imaging systems and methods that enable measurement of temperature distributions.

Improved thermal engineering can improve the operating characteristics and lifetimes of optoelectronic devices. For example, heating in semiconductor lasers can limit the maximum output power, shift the lasing wavelength, cause mode hopping, reduce lifetime, reduce the differential efficiency, increase the threshold current density, and limit the small signal modulation response. In addition, thermal stabilization of optoelectronic components is increasingly important to improving the performance of many photonic applications, such as wavelength division multiplexing and high-speed communications networks.

Furthermore, experimental exploration of the remarkably complex heat generation and transport processes in micro- or nano-structured optoelectronic devices such as diode lasers and semiconductor optical amplifiers is also challenging, in large part because the primary heat sources are often buried deep within these devices. Because of these difficulties, the thermal properties of optoelectronic devices are often thought of as bulk characteristics. For example, characterizations of semiconductor lasers such as optical spectra or power vs. current (LI) curves are often quoted at particular operating temperatures for the device as a whole, without detailed attention to the spatial heat distribution in the laser. These techniques are clearly insufficient when investigating nanostructured optoelectronic devices, since thermal variations occur on the submicrometer scale.

Thermoreflectance is a well-established non-contact method for measuring temperature distributions on a variety of different sample types. In the past decade, thermal imaging (as opposed to single point measurements) has become increasingly popular to measure surface temperature changes. As a result, different ways to achieve this goal have been published. Two-dimensional ("2-D") stochastic-resonance enhanced thermoreflectance imaging has been previously demonstrated with 250 nanometer ("nm") lateral spatial resolution and 10 milliKelvin ("mK") thermal resolution.

Thermoreflectance microscopy exploits the change in reflectance R of a material with temperature T:

$$\frac{\Delta R}{R} = \frac{1}{R} \cdot \frac{\partial R}{\partial T} \Delta T \equiv \kappa \cdot \Delta T$$

by measuring small changes in the reflectivity $\Delta R$, of a sample in response to temperature modulation $\Delta T$. Typical values of the thermoreflectance calibration coefficient range from $10^{-6}$ Kelvin$^{-1}$ ("K$^{-1}$") to $10^{-4}$ K$^{-1}$, so lock-in techniques are required to extract the temperature signal. The prior single-point measurements and scanning techniques can be replaced by 2-D imaging onto diode-arrays connected to multiple lock-in amplifiers or charge-coupled devices ("CCDs") with signal processing. However, until recently, it has been thought that the thermal resolution of imaging using a CCD is limited to 1 Kelvin ("K") by the quantization limit of the camera. This high-resolution 2-D thermal imaging technique can investigate both the thermal behavior of a range of optoelectronic devices and also, in combination with a total energy balance model, characterize the optical power distribution within working photonic integrated circuits and other active devices. However, because current sub-micrometer-resolution thermal imaging techniques offer little depth resolution, they are limited to surface imaging, and therefore cannot be used to investigate heat flow deep within a device.

Heat transport in optoelectronic devices is known to be severely degraded by large numbers of epitaxial interfaces and by the use of alloyed materials. Early work on thin films and superlattices demonstrated strong anisotropy in in-plane versus cross-plane thermal conductivity. Molecular dynamics simulations of heat flow in heterostructures suggest that even a single interface can decrease cross-plane thermal conductivity $\kappa_z$ by a factor of two; the presence of tensile strain further reduces $\kappa_z$. Furthermore, thermal conductivity can vary strongly with even small changes in material composition.

Thermal conductivity in superlattices is highly anisotropic and depends on a wide variety of factors, including interface quality, number of layers, layer thickness, lattice strain, and the ratio of the material composition. The cross-plane thermal conductivity $\kappa_z$ can be reduced by up to a factor of 10 by phonon reflections at interfaces. Small reductions in the in-plane thermal conductivity $\kappa_x$ also occur due to diffuse interface scattering. Results for GaAs/AlAs have shown that while the cross-plane thermal conductivity can be less even than the corresponding alloy value, the in-plane thermal conductivity of a GaAs/AlAs superlattice is usually less than that of the bulk materials but greater than that of the corresponding alloy.

In general, poor heat transport across heterojunctions results in relatively low thermal conductivities for complex optoelectronic devices. In particular, vertical cavity surface-emitting lasers ("VCSELs") have a high thermal resistance due to their small size and the poor thermal conductivity of the mirrors (e.g., DBR mirror), so remarkably large variations (up to 200° C.) in the internal temperature distribution are predicted, both radially across the active region and vertically along the optical axis. In addition, prior work has shown radial surface temperature variations of up to 5 K between the center and edge of an operating VCSEL. Thermal models of edge-emitting lasers predict large variation in thermal impedance across the plane of the active region, resulting in temperature variations of up to 40%. Other work on quaternary blue-green lasers predicts temperature differences between surface and active region of 0.1-0.5 K for p-side up lasers and 1.5 K for p-side down devices.

A wide range of alternative methods for 2-D surface temperature measurements have been developed. A comparison of several temperature measurement techniques is found in FIG. 1, several of which are discussed below. Liquid crystal ("LC") thermography provides good spatial and temperature resolution (1 micrometer ("µm") and 0.05 to 0.5 K), but temperatures can only be measured relative to the clearing point temperature at which the crystals undergo a phase transition. Fluorescent microthermography is a similar thermal imaging technique with better temporal resolution; both of these methods require thin film deposition on the surface of the test device. Optical interferometry based on thermal expansion provides micrometer scale measurements with extremely good thermal resolution ($10^{-6}$ K), but calibration of temperature based on surface displacement is very difficult for materials without a high thermal expansion coefficient. Scanning thermal microscopy can achieve a spatial resolution of 50 nm; this technique typically uses an atomic force microscope as a measurement platform.

The ability to measure temperature inside a three dimensional structure is currently very limited. Because Si and InP are transparent in infrared ("IR") measurements ($\lambda > 2$ μm), it is possible to use near-IR thermography to image flip-chip bonded ICs through the substrate; however, the lateral resolution is limited to 5 μm.

CCD thermoreflectance has been performed using the imaging optics of a widefield microscope, for which there is little depth discrimination and the Rayleigh criterion puts a lower limit on lateral spatial resolution of $dx = 0.6\lambda/NA$ where $\lambda$ is the illuminating wavelength and NA is the numerical aperture of the microscope objective. Widefield microscopy has proven adequate for imaging the temperature distribution across the surface of a number of active optoelectronic devices, including semiconductor optical amplifiers, edge-emitting and surface-emitting diode lasers. However, accurate investigation of heat transport above and below dielectric layers (e.g., oxide passivation layers), across semiconductor interfaces (e.g., multi-quantum well active regions), or for devices with features less than 250 nm or alternatively offering poor image contrast demands further improvement in lateral and vertical spatial resolutions.

Therefore, there is a need for methods and systems for performing confocal thermoreflectance measurements that can measure temperature from reflective layers, objects, or defects, or for devices with features less than 250 nm or alternatively offering poor image contrast (e.g., devices such as transistors, nanocircuits, etc).

There is also a need for profiling thermal distribution both within an operating device, including LEDs, edge-emitting lasers, and VCSELs signal, and at the surface, heat sink, and sides, so that both the internal distribution and boundary conditions are understood.

SUMMARY

Disclosed herein are thermoreflectance imaging methods.

An embodiment of a method of performing thermoreflectance measurements with an imaging system comprises: reflecting radiation from a number of points in a sample in response to an illuminating radiation while a temperature modulation is applied to the sample; acquiring digital images of the reflected radiation after the reflected radiation passes through an aperture; and deriving a map of relative reflectivity of the sample based on the digital images. At least a portion of the illuminating radiation passes through at least a portion of the sample and is reflected at a change refractive index interface.

Another method of performing thermoreflectance measurements comprises: modulating temperature of a sample at a selected modulation frequency (f); illuminating a portion of the sample with radiation; passing at least a portion of the illuminating radiation into the sample; reflecting at least a portion of the passing radiation at a change refractive index interface; rejecting non-focused light using an aperture; utilizing an imaging system to detect the reflecting radiation, wherein the imaging system obtains a selected number of reflectance images in one period of the temperature modulation; calculating from the reflectance images a quasi three-dimensional map of the sample.

The above described and other features are exemplified by the following Figures and detailed description.

BRIEF DESCRIPTION OF THE DRAWINGS

Embodiments will now be described by way of example only, with reference to the accompanying drawings which are meant to be exemplary, not limiting, and wherein like elements are numbered alike in several Figures, in which:

FIG. 1 is a table of thermal imaging techniques.

DETAILED DESCRIPTION

Figure 2:
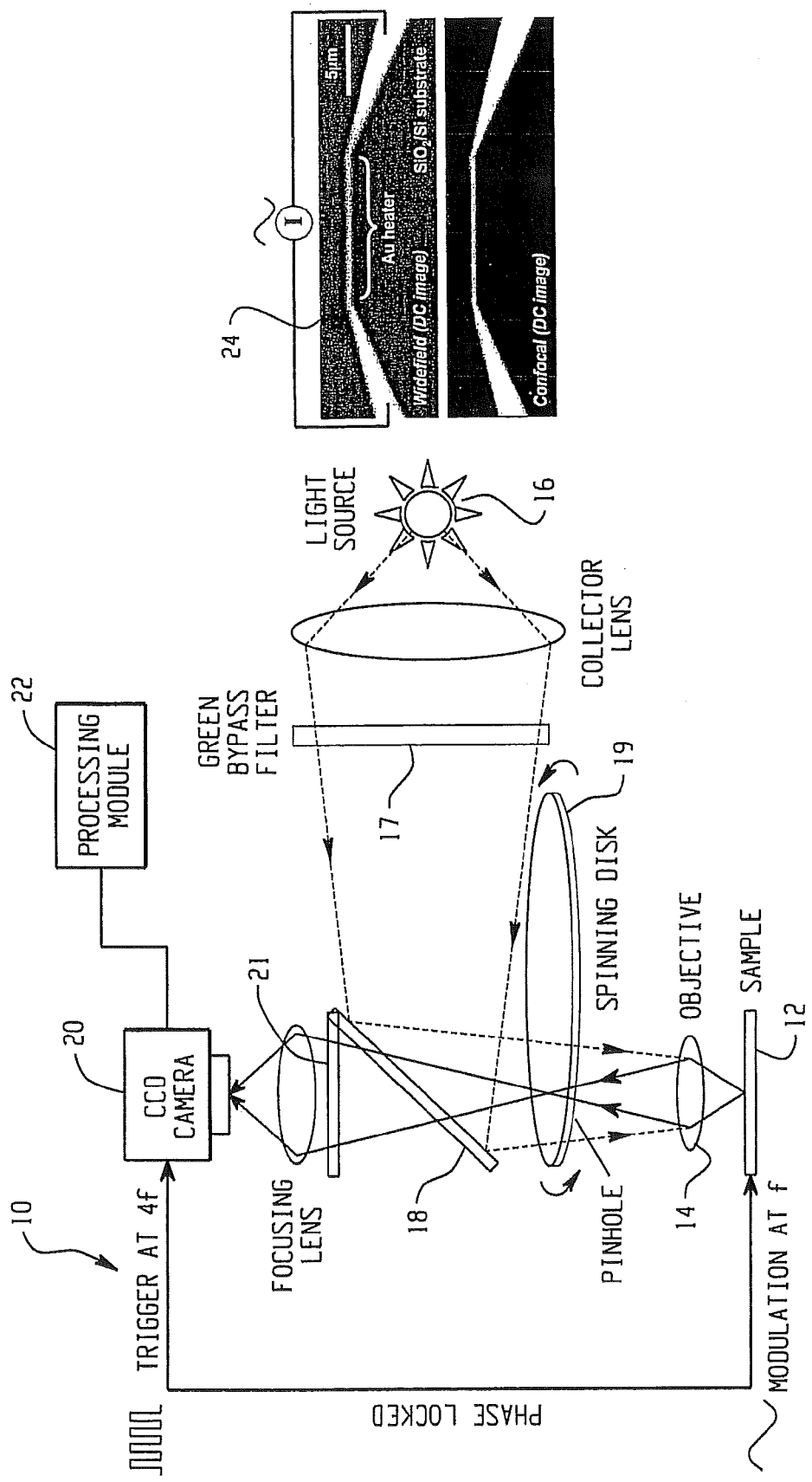
FIG. 2 is a confocal Nipkow spinning disk thermoreflectance setup (left) and widefield and confocal DC images of gold heater pattern used to characterize resolution (right).

Stochastic resonance can be used to beat the quantization limit of the camera, resulting in a two orders of magnitude improvement in the thermal resolution. Additionally, the 2-D, CCD-based, stochastic resonance enhanced thermoreflectance imaging technique can achieve a 10 mK thermal resolution.

The present method can be used for both thermal characterization of electronic, optoelectronic, and/or photonic devices, both at the surfaces and within an operating device, including imaging through transparent packaging. The method enables the production of a quasi three-dimensional ("3-D") thermal characterization of the heat signature. In other words, at each interface of adjacent, different, refractive indices (e.g., at the top surface, at the bottom surface, at the interface of adjacent layers wherein the layers have different refractive indices, and so forth, also referred to as the "RI interface") a portion of the light is reflected back. The light that is reflected back can be captured and employed to determine the heat signature of the component at that point. From the results a quasi 3-D thermal characterization can be formed. This method can be applied to a wide range of applications wherein the article has a sufficient degree of optical transmission to allow an adequate amount of light to be reflected from RI interface(s) (e.g., from the bottom surface through the article) to enable the present thermal characterization. (It is understood that a "sufficient amount" is based upon the sensitivity of the data acquisition device.) For example, articles can include photonic and optoelectronic devices (e.g., lasers, optical amplifiers, photovoltaics, solar cells, etc.), electronics (e.g., transistors, integrated circuits, etc.), and materials characterization (e.g., advanced composites, metals, ceramics, etc.). Application to electronic devices and circuits includes characterization of hot spots, defects, or other performance markers, from either side of a chip, including imaging through the substrate or examining a flip-chip bonded device. It can also be applied to general characterization of materials and structures, including mapping thermal conductances, identifying defects or delaminations, locating subsurface cracks, or identifying inclusions or contaminants.

The thermoreflectance apparatus and methods disclosed herein combine high lateral spatial resolution (e.g., a resolution of at least 250 nanometers (nm)) and high vertical spatial resolution (e.g., a resolution of at least 1 micrometer (μm)) with a temperature resolution of 10 mK. This combination opens the door to new applications, such as: the non-invasive, quasi 3-D thermal profiling inside operating optoelectronic devices; the analysis of heat transport in complex optoelectronic devices; the ability to image transparent devices; and the ability to determine mechanisms for internal heat generation in homojunctions and heterostructured devices. The temperature map can exhibit a lateral spatial resolution of 100 nanometers to 1 micrometer, specifically, 100 nm to 500 nm, and more specifically, 100 nm to 200 nm; and/or a vertical spatial resolution of 100 nanometers to 1 micrometer, specifically, 350 nm to 750 nm, and more specifically, 500 nm to 600 nm.

FIG. 2 schematically illustrates an embodiment of an apparatus 10 for measuring thermoreflectance of a sample 12, for example, an operating semiconductor device. A microscope objective 14 focuses light generated by a light source 16 and directed to the microscope via a beam splitter 18, onto the sample 12, e.g., through aperture(s) in the disk (19). CCD camera 20 detects the backreflected light from the sample 12 which passes through the optical filter 21. A bandpass filter 17 can be employed to allow passage of particular wavelength(s) of light to pass from the light source to the sample. The backreflected light from the sample 12 can be passed through aperture(s) to, for example, reject non-focused light, enabling the receipt and characterization of light that has been reflected back from all or a portion of the sample 12. The aperture(s) can provide a slight improvement in lateral spatial resolution over traditional widefield light microscopes; e.g., using the Rayleigh criterion, the lower limit of the lateral spatial resolution of a confocal microscope is $\Delta r = 0.32 \lambda / NA$. The vertical resolution for an air-immersion setup can be approximated by the 3 dB defocusing distance $d_z(3 \text{ dB}) = 0.45 \, n\lambda/(1-\cos\theta)$, where n is the refractive index of the sample and $NA = \sin\theta$ is the numerical aperture of the microscope. Hence, using a high NA objective (NA≈1) and a 450 nm probe beam to image GaN (n≈2.7), lateral and axial spatial resolutions of 150 nm and 550 nm would be expected, respectively. Further improvements in resolution are potentially obtainable using oil immersion lenses or 4Pi confocal microscopy, which has been demonstrated to offer a 3 to 5 times improvement in the axial resolution. 4Pi confocal microscopy has been shown to provide axial resolution down to approximately 100 nm. Improvement in lateral resolution can also potentially be obtained using near-field scanning optical microscopy (NSOM), which has shown lateral resolution on the order of $\lambda/40$ (greater than 15 nm). As an alternative to confocal microscopy, thermoreflectance using structured illumination microscopy could be used to achieve similar axial and lateral resolutions.

Confocal microscopy can use a single aperture (e.g., pinhole) or an array of apertures (e.g., a disk having an array of apertures) in order to exclude light that is not at the microscope's focal plane. With a single aperture, confocal microscopy is fundamentally a single-point technique, using only a single-pixel detector and a lock-in amplifier at the microscope output. To obtain a two dimensional ("2-D") lateral image in the desired focal plane, an aperture scanning confocal microscope raster scans the beam across the sample and reconstructs the image. Alternatively, real-time, 2-D confocal images at the desired depth can be obtained using an aperture mask or a microlens-enhanced Nipkow disk (a spinning mask of apertures) in combination with a CCD detector and the signal processing lock-in techniques discussed above.

The aperture(s) can have a diameter (i.e., the shortest diameter) of less than or equal to 100 μm, specifically, 15 μm to 75 μm, more specifically, 25 μm to 50 μm. For example, the spinning disk 19 can be chrome-plated glass with aperture array(s) wherein different arrays can have different diameter aperture(s) and/or different diameter aperture(s) can be employed within an array. The size of the aperture(s) can be chosen to enable the passage of the desired wavelength of backreflected light while excluding other light. For example, disk or barrier can have two aperture arrays, one with 25 μm diameter apertures, the other with 45 μm diameter apertures. Alternatively, or in addition, an optical fiber can be coupled to receive the backreflected light. It is noted that the apertures can have various geometries, e.g., circular (e.g., pinhole), slit (such as elongated, oval, or the like), Relative motion between the sample 12 and the apparatus 10 allows the desired series of images to be obtained. For example, the aperture(s) can be located in a (i) spinning disk 19 used to provide confocal imaging where backreflected light from locations other than the focal plane is excluded, (ii) in a barrier between the data acquisition device (e.g., camera) and the sample. When the aperture(s) are located in the barrier, relative motion is established between the sample 12 and the apparatus 10 by moving the sample 12 and/or the apparatus 10. For example, for the Nipkow disk, the sample remains stationary during the measurement and the disk spins. Each pinhole in the disk acts as a single point measurement and, as the disk spins, the multiple points of light sweep across sample to create a full image of the sample at the focal plane.

The light source 16 can be an LED, a laser, an arc lamp or other source, as well as a combination comprising at least one of the foregoing light sources. The wavelength of the light source 16 can be chosen to meet specific sample material considerations.

The sample 12 can be temperature-modulated at a selected modulation frequency (f), where the sample 12 is periodically heated and cooled by employing, e.g., an electrical current applied to the sample, modulated laser beams absorbed by the sample, temperature changes of the sample mount, inductive heating, as well as a combination comprising at least one of the foregoing. A multi-channel lock-in technique can be utilized to detect the reflected light by the CCD camera 20. As discussed in more detail below, the camera is triggered at a frequency that is multiple times the frequency of the temperature modulation (e.g., four times the temperature modulation frequency) to acquire multiple (e.g., four) images within a period (T) of the sample modulation. For example, number of acquired images can be greater than $10^3$, specifically, greater than $10^6$, and more specifically, $4 \times 10^3$ to $8 \times 10^6$. The data collected by the CCD camera can be transferred to a processing module 22 for analysis.

The specific camera is dependent upon the desired resolution. For example, in some embodiments, the camera can be a 12 bit grayscale CCD, which can deliver up to 60 frames per second through a USB2.0 bus, and has 652 by 494 pixels. Pipelining allows the collection of individually externally triggered images while maintaining a high duty cycle of more than 98%. A digital lock-in method, commonly referred to as 4 bucket method can be employed, where four images per period T of the sample modulation are acquired and summed pixel by pixel. It is, however, understood that the apparatus is not limited to the specific camera, communications bus, or other exemplary parameters (e.g., frames/second, number of pixels) employed in this illustrative embodiment. For example, an analog detector with a lock-in amplifier (or array of analog detectors with lock-in amplifiers) can be used.

The four images $I_k$, k=1 ... 4, which stem from the time integration of the signal with subsequent truncation of sub-threshold signal contributions, can be represented mathematically as follows:

$$I_k = \sum_{i=1}^{N} \left[ \frac{4}{T} \int_{\frac{(4i+k-1)T}{4}}^{\frac{(4i+k-1)T}{4}} \left( c + \Delta\cos(\omega t + \varphi) \pm \frac{4}{2\pi}\delta \right) dt \right], k \in \{1, 2, 3, 4\} \quad (1)$$

wherein: c represents the time independent signal (e.g., the average brightness detected by the CCD), $\Delta$ is its modulation, $\delta$ is the noise, t is the elapsed time from the start of measurement, $\omega$ is the angular frequency of the modulation, and $\phi$ is the phase. The relative variation of the signal $\Delta R/R$ and the phase $\hat{\phi}$ can be recovered. However, the equations for $\Delta R/R$ and $\hat{\phi}$ are written below with a particular emphasis on the uncertainty since it allows formulating a criterion for successful data acquisition (as discussed below):

$$\left| \frac{\Delta R}{R} \right| = \frac{\pi}{\sqrt{2}} \frac{\sqrt{(I_1 - I_3)^2 + (I_2 - I_4)^2}}{I_1 + I_2 + I_3 + I_4} = \frac{\Delta \pm \delta}{c} \quad (2)$$

$$\phi = \arctan\left( \frac{I_1 + I_2 - I_3 - I_4}{I_1 - I_2 - I_3 + I_4} \right) = \arctan\left( -\frac{\Delta\sin(\phi) \pm \delta}{\Delta\cos(\phi) \pm \delta} \right) \quad (3)$$

wherein c is the average brightness detected by the CCD, $\Delta T$ is the change in temperature, $\Delta R$ is the change in reflectivity, and thus, $\Delta R/R$ is, effectively, the temperature signal for a given point/pixel.

The specific camera is dependent upon the desired resolution. For example, in some embodiments, the camera can be a 12 bit grayscale CCD, which can deliver up to 60 frames per second through a USB2.0 bus, and has 652 by 494 pixels. Pipelining allows the collection of individually externally triggered images while maintaining a high duty cycle of more than 98%. A digital lock-in method, commonly referred to as 4 bucket method is employed, where four images per period T of the sample modulation are acquired and summed pixel by pixel. It is, however, understood that the apparatus is not limited to the specific camera, communications bus, or other exemplary parameters (e.g., frames/second, number of pixels) employed in this illustrative embodiment.

These equations can be evaluated for each individual pixel (for example using the four CCD image measurements (I1, I2, I3, and I4), thus generating quasi 3-dimensional maps of both the signal magnitude and the phase when combined with the optical sectioning capability of confocal microscopy. The noise in the CCD images can stem from signal, independent of thermal and readout noise, and from the signal-dependent shot noise. Because the signal is normalized for each pixel individually, the otherwise important photo-response non-uniformity noise (the most significant component of pattern noise) does not influence the noise in the $\Delta R/R$ image. As has been confirmed experimentally that uncertainty in $\Delta R/R$ can be expressed by the following relation:

$$\sigma_{\Delta R/R}(c, N) = \frac{1}{\sqrt{N}} \left( \frac{A}{\sqrt{c}} + \frac{B}{c} \right) \equiv \frac{16}{2\pi T} \int_0^{T/4} \delta dt, \quad (4)$$

where N is the number of series of 4 images (iterations), and c is the average brightness of the CCD signal (compare equation (1)). Equation (4) can serve as a definition of the noise term $\delta$ used in equations (1-3).

As discussed in more detail below, the acquisition of images within each temperature modulation cycle can be iterated a sufficient number of times (e.g., $10^6$ iterations) to allow detection of signals that are smaller than the detector's bit-depth. In other words, noise induced threshold crossing phenomenon can be employed to enhance the detection signal-to-noise—via a sufficiently large number of iterations—beyond a level that has been traditionally considered feasible.

Using equation (4) above, a plot of the experimental uncertainty as a function of the number of iterations N and the average number of CCD counts c can be generated. The plot can easily be adapted for any other model once the coefficients A and B have been measured. Nevertheless, the general features will remain the same. The plot can indicate that the best experimental accuracy can be achieved by using a detector with a high bit depth and operating it close to saturation intensity.

In addition, this map indicates that a large number of iterations permits the detection of signals several orders of magnitude smaller than the bit-depth of the detector, for example, signals with a measured uncertainty that is smaller than $2 \cdot 10^{-6} = \frac{1}{2}^{19}$ using the 12 bit CCD mentioned above. This is two orders of magnitude better than the standard considerations and published experimental conditions, which estimate the uncertainty to be at least $\frac{1}{2}^{12} = 2.5 \cdot 10^{-4}$.

By way of further illustration, the following example can be considered. A gold surface has a thermoreflectance coefficient $\kappa = 3.3 \cdot 10^{-4}$ K$^{-1}$ for an illumination wavelength of 467 nm. Based on this number, the temperature resolution can be calculated as $\Delta T = \kappa^{-1} \Delta R/R$. This means that instead of being able to resolve temperature changes with an uncertainty of 1K per pixel, the improved method permits the measurement with uncertainties smaller than 10 milliKelvin (mK) per pixel.

To determine the probe wavelength to maximize the thermoreflectance signal, it is desirable to know the material-dependent bounds on possible probe wavelengths (e.g., the wavelengths wherein there is a sufficient degree of optical transmission to allow a sufficient amount of light to be reflected from all RI interface(s) to enable the present thermal characterization).

Figure 3:
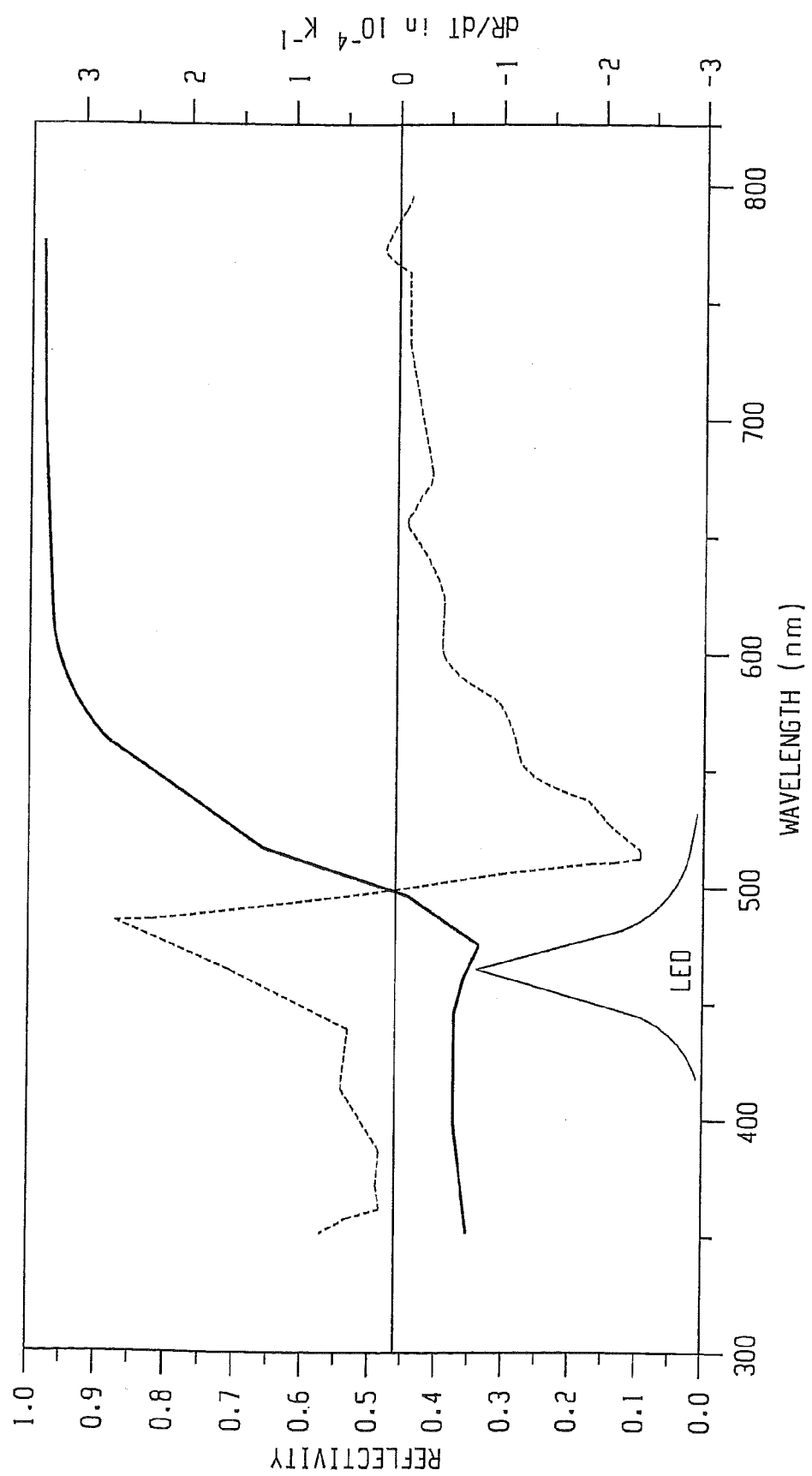
FIG. 3 is a plot of data for determining probe wavelength of thermoreflectance measurements of gold.

The device structure and material composition determines the choice of wavelength for the probe beam. In order to enhance the thermoreflectance signal $\Delta R/R$, the wavelength of the probe beam can be chosen to operate at a resonance of dR/dT for the material, while minimizing the overall reflectivity R in part to avoid carrier recombination at the focal plane due to absorption of the probe beam. FIG. 3 illustrates this choice for gold. Hence, the energy of the probe beam can be slightly greater than the bandgap energy of the material to be measured. In contrast, the probe beam energy can be less than the bandgap energy of any overlaying material in order to achieve transparency. Having established the material-dependent bounds on possible probe wavelengths ($\lambda_{top\_layer} < \lambda_{probe} < \lambda_{sample\_layer}$), the choice of wavelength is further refined (enhance dR/dT while reducing R) by spectroscopically resolving the reflectance R and the dR/dT signal to obtain plots such as that contained in FIG. 3 for precise experimental conditions.

In order to compare the performance of widefield and confocal thermoreflectance, a resolution target comprising a gold heater was fabricated on silicon substrate, on top of a 1 μm thick thermally grown silicon dioxide (SiO$_2$) layer. The heater 24 shown in FIG. 2 comprises a 10 µm long gold wire that is 50 nm thick and 500 nm wide. The wire was connected at both ends to a large gold pad for electrical probing, which allows joule heating through current injection.

Figure 4:
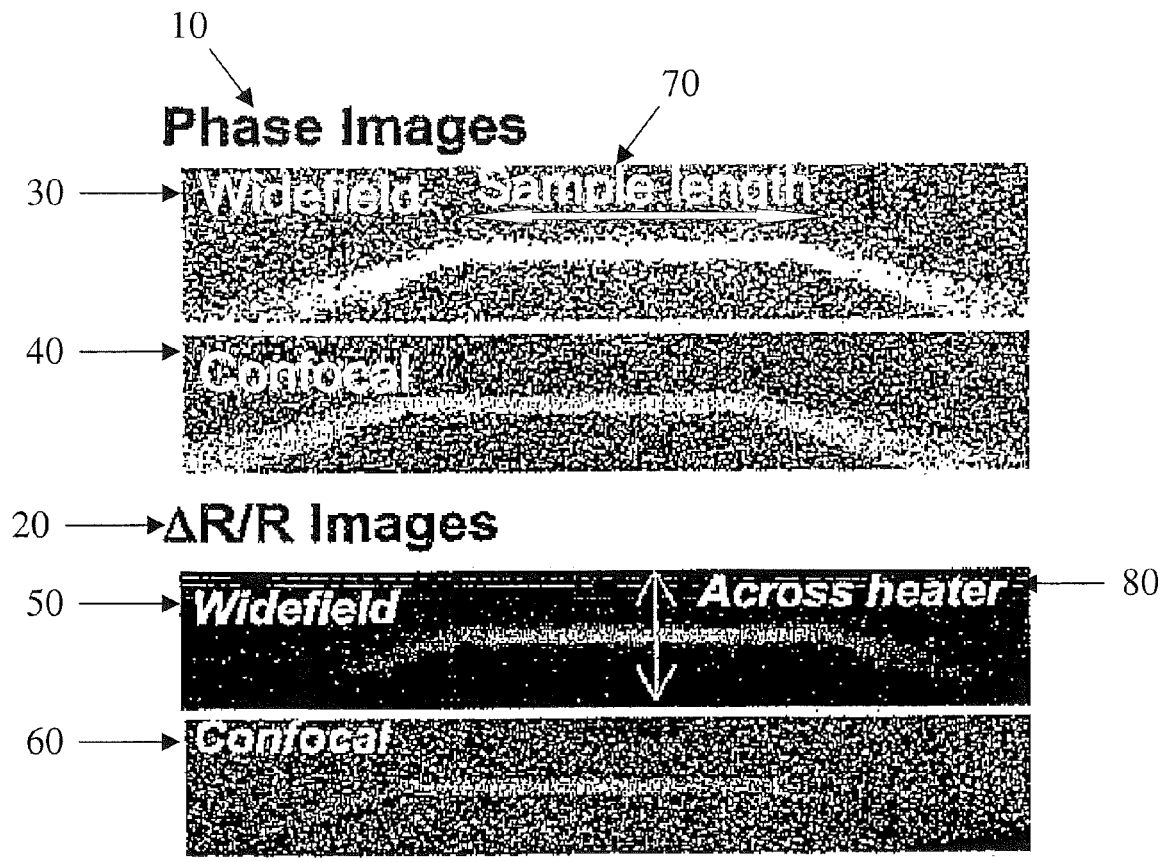
FIG. 4 is widefield and confocal thermoreflectance images showing phase and DR/R of the gold heater with a dissipated power of 10.6 mW.
Figure 5:
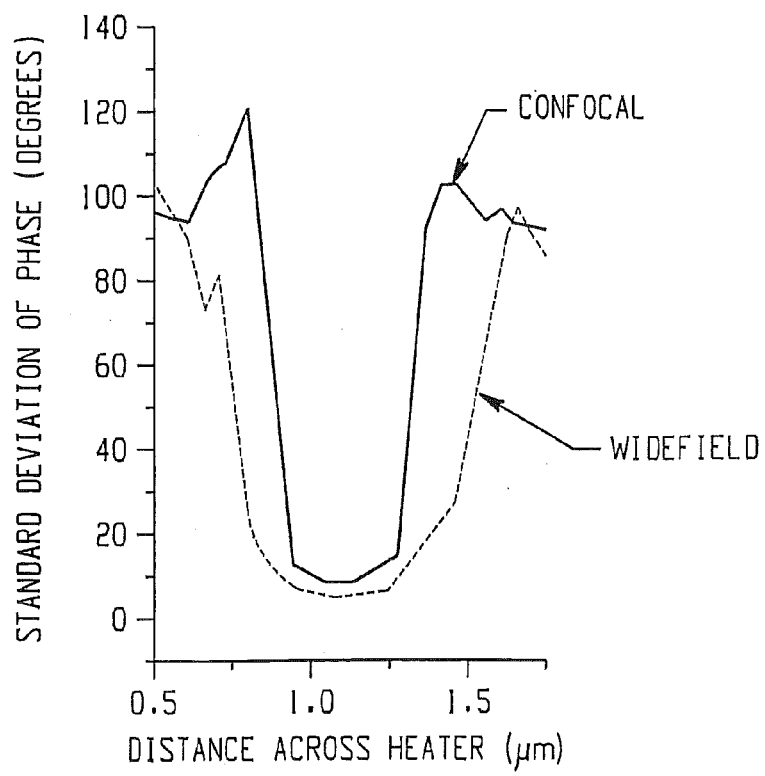
FIG. 5 is a plot of the standard deviation of the phase along the length of the heater, as a function of distance across the heater.
Figure 6:
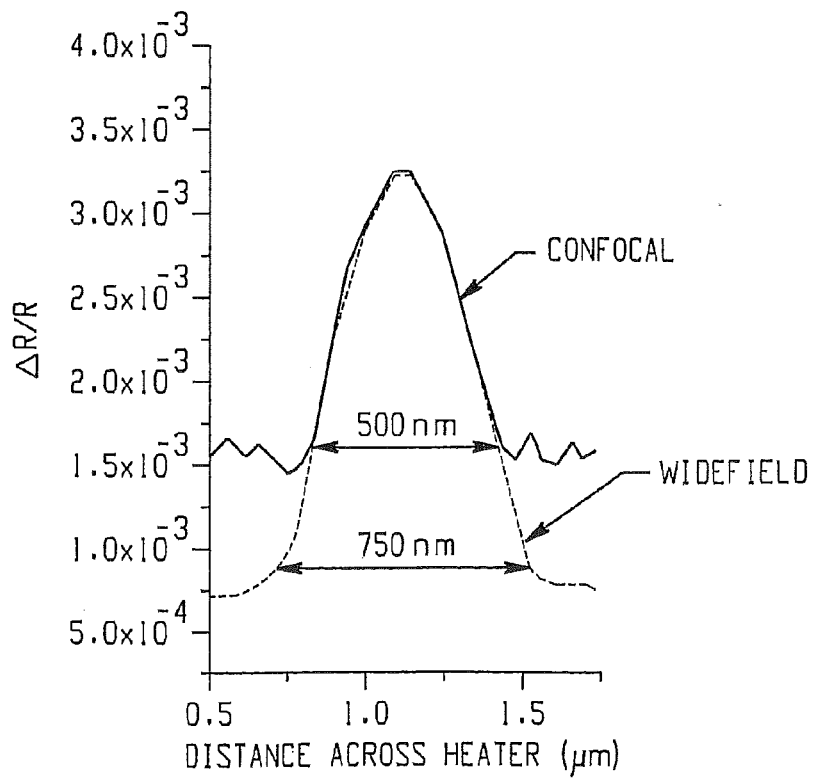
FIG. 6 is a plot of the average $\Delta R/R$ along the length of the heater, as a function of distance across the heater.

The gold wire heater was modulated by a square wave current source at a frequency of 10 Hz, and images were captured using a CCD exposure time of 24 milliseconds (ms). For a current of 7.5 milliamperes (mA), approximately 10.6 milliwatts (mW) was dissipated in the heater ($R_{heater} \approx 190\Omega$), and both widefield and confocal thermoreflectance measurements were taken. Image of both the phase and ΔR/R measurements of the 500 nm-wide heater are shown in FIG. 4, allowing comparison between the two imaging modes. As shown in FIG. 4, the confocal mode (40, 60) is visibly sharper in both the phase (10) and ΔR/R (20) images compared to the widefield mode (30, 50), and the edge of the heater can easily be distinguished in the confocal ΔR/R image (60). The sample length (70) is indicated in widefield mode (30), while the distance across the heater (80) is indicated in widefield mode (50). The degree of improvement is quantified in the FIGS. 5 and 6. For FIG. 6, the standard deviation of the phase has been taken for each row along the length of the heater, and then plotted as a function of distance across the heater. A small standard deviation is consistent with a strong thermoreflectance signal, and for the confocal case, it can be seen that the quality of the signal degrades more quickly from the center of the wire, compared to the widefield measurement. This is attributed to the improved contrast and suppression of light from the Si substrate below the $SiO_2$ layer. In FIG. 6, the ΔR/R has been averaged along the length of the wire. The wire boundary can clearly be seen in the confocal case, and the width of the thermoreflectance signal corresponds well to the wire width of 500 nm. For the widefield case, there is no suppression of light from the substrate and the thermal signal extends to a width of 750 nm or 50% greater than the known width of the wire.

The above exemplary embodiments present at least three significant improvements for CCD based thermoreflectance microscopes. One of the improvements enables the non-invasive thermal profiling inside operating optoelectronic devices. A second improvement is the ability to analyze heat transport in complex optoelectronic devices. Yet another improvement is the ability to determine mechanisms for internal heat generation in homojunctions and heterostructured devices. Because of these features, the above thermoreflectance technique enables new applications that were previously unattainable. Further, these teachings are not limited to CCD detectors, but can be practiced with other imaging systems (e.g., digital imaging systems and/or analog imaging systems), such as CMOS imaging detectors, analog detectors, and so forth.

One embodiment of a method of performing thermoreflectance measurements with an imaging system comprises: reflecting radiation from a number of points in a sample in response to an illuminating radiation while a temperature modulation is applied to the sample; acquiring digital images of the reflected radiation after the reflected radiation passes through an aperture; and deriving a map of relative reflectivity of the sample based on the digital images. At least a portion of the illuminating radiation passes through at least a portion of the sample and is reflected at a change refractive index interface.

In one embodiment, a method of performing three-dimensional thermoreflectance measurements comprises: modulating temperature of sample at a selected modulation frequency $f_1$; illuminating a portion of the sample with radiation modulated at a different frequency $f_2$; rejecting non-focused light using an aperture; utilizing a digital imaging system to detect radiation reflected from the sample, modulated at a difference frequency equal to a difference of the f1 and f2 frequencies in response to the illumination to generate reflectance images of the sample, wherein the imaging system is triggered to obtain a selected number of reflectance images in one cycle of the oscillation of the intermediate frequency; calculating from the images a map of relative reflectance changes of the sample; and iterating the step of acquiring reflectance images of a sufficient number of oscillation cycles at the difference frequency, so as to obtain a sufficiently small uncertainty in the calculated relative reflectance change such that signals smaller than the bit-depth of the digital imaging system can be detected.

In yet another embodiment, a method of performing thermoreflectance measurements can comprise: acquiring digital images of radiation reflected from a number of points through a aperture for a sample in response to an illuminating radiation while a temperature modulation is applied to the sample; deriving a map of relative reflectivity of the sample volume based on the images; and optionally repeating acquisition of images (e.g., digital images) until uncertainty in the relative reflectivity is reduced to a value such that relative reflectivity signals that are less than a bit-depth of the imaging system can be detected.

The embodiments can further comprise calculating a relative temperature map of the sample based on the relative reflectance map. The relative temperature map exhibits a temperature resolution in a range of 1 mK to 1 Kelvin, specifically, 10 mK to 25 mK. The imaging system can include a single-point confocal microscope, a widefield microscope, optical fiber based confocal microscope, and/or a scanning confocal microscope. The thermoreflectance technique can be performed with various imaging, such as single point confocal measurements, scanning confocal imaging, Nipkow disk imaging, an aperture mesh, as well as combinations comprising at least one of the foregoing. The imaging system can detect radiation using 4Pi confocal microscopy, near-field scanning optical microscopy, and/or structured illumination microscopy. The imaging system can comprise oil immersion lens(es). The radiation source can be an LED, a LASER, and/or an arc lamp, and the system can further comprise a bandpass filter.

The methods disclosed herein enable numerous advantages including enhancement in lateral spatial resolution, improvement in the image contrast (thereby enabling viewing of a greater number of material, such as a silicon. structure on oxidized material), and/or quasi 3-D imaging (as well as 1 dimensional and 2 dimensional imaging).

Ranges disclosed herein are inclusive and combinable (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The suffix "(s)" as used herein is intended to include both the singular and the plural of the term that it modifies, thereby including one or more of that term (e.g., the aperture(s) includes one or more apertures). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

Those having ordinary skill in the art will also appreciate that various modifications can be made to the above embodiments without departing from the scope of the invention.

We claim:

1. A method of performing thermoreflectance measurements with an imaging system, comprising:
    reflecting radiation from a number of points in a sample in response to an illuminating radiation while a temperature modulation is applied to the sample, wherein at least a portion of the illuminating radiation passes through at least a portion of the sample and is reflected at a change in refractive index interface;
    passing the reflected radiation through an aperture that rejects non-focused light;
    acquiring digital images of the reflected radiation after the reflected radiation passes through the aperture; and
    deriving a map of relative reflectivity of the sample based on the digital images.

2. The method of claim 1, further comprising repeating acquisition of digital images until uncertainty in the relative reflectivity is reduced to a value such that relative reflectivity signals that are less than a bit-depth of the imaging system can be detected.

3. The method of claim 1, further comprising selecting the number of acquired digital images to be greater than $10^3$.

4. The method of claim 1, further comprising selecting the number of acquired digital images to be $4 \times 10^3$ to $8 \times 10^6$.

5. The method of claim 1, wherein the reflected radiation passes through a confocal spinning disk.

6. The method of claim 5, wherein the spinning disk is a Nipkow spinning disk having an array of apertures that reject non-focused light.

7. The method of claim 1, wherein the imaging was selected from the group consisting of single point confocal measurement imaging, scanning confocal imaging, Nipkow disk imaging, an aperture mesh, as well as combinations comprising at least one of the foregoing.

8. The method of claim 1, using an analog detector with a lock-in amplifier.

9. The method of claim 1, wherein the aperture comprises a geometry selected from the group consisting of circular, slit, and combinations comprising at least one of the foregoing.

10. The method of claim 9, wherein the aperture comprises a geometry selected from the group consisting of pinhole, elongated, oval, and combinations comprising at least one of the foregoing.

11. The method of claim 1, wherein the sample comprises a transparent sample.

12. The method of claim 1, wherein the map exhibits a lateral spatial resolution of 100 nanometers to 1 micrometer.

13. The method of claim 1, wherein the aperture comprises an array of apertures that reject non-focused light.

14. The method of claim 1, wherein the illuminating radiation passes through the aperture before contacting the sample.

15. A method of performing thermoreflectance measurements, comprising:
    modulating temperature of a sample at a selected modulation frequency (f);
    illuminating a portion of the sample with radiation;
    reflecting at least a portion of the radiation;
    rejecting non-focused light using an aperture;
    utilizing an imaging system to detect the reflecting radiation, wherein the imaging system obtains a selected number of reflectance images in one period of the temperature modulation;
    calculating from the reflectance images a map of the sample.

16. The method of claim 15, wherein uncertainty in the calculated relative reflectance is less than $10^{-5}$.

17. The method of claim 15, further comprising passing at least a portion of the illuminating radiation into the sample and reflecting at least a portion of the passed radiation at a change refractive index interface.

18. The method of claim 15, wherein the map is a quasi 3-D characterization.

19. The method of claim 15, wherein the imaging system detects radiation using 4Pi confocal microscopy.

20. The method of claim 15, the digital imaging system detects radiation using near-field scanning optical microscopy.

21. The method of claim 15, wherein the imaging system detects radiation using structured illumination microscopy.

22. A method of performing thermoreflectance measurements with an imaging system, comprising:
    reflecting radiation from a number of points in a sample in response to an illuminating radiation while a temperature modulation is applied to the sample, wherein at least a portion of the illuminating radiation passes through at least a portion of the sample and is reflected at a change refractive index interface;
    passing the reflected radiation through an optical fiber that rejects non-focused light;
    acquiring digital images of the reflected radiation after the reflected radiation passes through the optical fiber; and
    deriving a map of relative reflectivity of the sample based on the digital images.

23. A method of performing thermoreflectance measurements with an imaging system, comprising:
    passing illuminating radiation through an aperture and into a sample while a temperature modulation is applied to the sample, wherein at least a portion of the illuminating radiation is reflected at a change refractive index interface;
    reflecting radiation from a number of points in a sample;
    passing the reflected radiation through the aperture which rejects non-focused light;
    acquiring digital images of the reflected radiation; and
    deriving a map of relative reflectivity of the sample based on the digital images.

24. The method of claim 23, wherein the digital images are taken at the same location in the sample.

25. A method of performing thermoreflectance measurements with an imaging system, comprising:
    reflecting radiation from a point in a sample in response to an illuminating radiation while a temperature modulation is applied to the sample, wherein at least a portion of the illuminating radiation passes through at least a portion of the sample and is reflected at a change in refractive index interface;
    passing the reflected radiation through an aperture that rejects non-focused light;
    acquiring digital images of the reflected radiation after the reflected radiation passes through the aperture; and
    deriving a map of relative reflectivity of the sample based on the digital images.

26. The method of claim 25, wherein the radiation is reflected from a single point.

* * * * *